United States Patent
Zhao et al.

(10) Patent No.: US 8,349,845 B2
(45) Date of Patent: Jan. 8, 2013

(54) THIAZOLOPYRIMIDINES FOR USE IN THERAPY

(75) Inventors: Fei-Yue Zhao, Coventry (GB); Alistair Kerr Dixon, London (GB); Jonathan Mark Treherne, Coventry (GB); Chizuko Koseki, London (GB); Kevin Lee, Coventry (GB); David Spanswick, Coventry (GB)

(73) Assignee: Sosei Group Corporation, Tokyo (JP)

( * ) Notice: Subject to any disclaimer, the term of this patent is extended or adjusted under 35 U.S.C. 154(b) by 574 days.

(21) Appl. No.: 11/917,425

(22) PCT Filed: Jun. 19, 2006

(86) PCT No.: PCT/GB2006/002248
§ 371 (c)(1),
(2), (4) Date: Dec. 10, 2009

(87) PCT Pub. No.: WO2006/136806
PCT Pub. Date: Dec. 28, 2006

(65) Prior Publication Data
US 2010/0216819 A1 Aug. 26, 2010

(30) Foreign Application Priority Data
Jun. 20, 2005 (GB) .................................. 0512554.7

(51) Int. Cl.
*A61K 31/519* (2006.01)
*A61K 43/00* (2006.01)
*A61K 31/535* (2006.01)

(52) U.S. Cl. .............. 514/259.2; 514/211.13; 514/232.5

(58) Field of Classification Search ................. 514/777
See application file for complete search history.

(56) References Cited

FOREIGN PATENT DOCUMENTS

| EP | 0050671 | * | 4/1980 |
| EP | 0 050 671 | | 5/1982 |

OTHER PUBLICATIONS

Database CA, Chemical Abstracts Service, JP 55 064591, May 15, 1980, "Thiazolo[3,2-a]pyrimidine derivatives," Database Accession No. 1981:30781.

Database CA, Chemical Abstracts Service, JP 55 066592, May 20, 1980, "7-Alkoxythiazolo[3,2-a]pyrimidine derivatives," Database Accession No. 1981:15764.

Komoriya et al., "Anti-Arthritic and Immunoregulatory Effects of TI-31 on Collagen-Induced Arthritis," *Japan J. Pharmacol.*, 1987, vol. 45, pp. 389-396.

* cited by examiner

*Primary Examiner* — Sreeni Padmanabhan
*Assistant Examiner* — Timothy E Betton
(74) *Attorney, Agent, or Firm* — Saliwanchik, Lloyd & Eisenschenk

(57) ABSTRACT

Use of a compound of formula (I) wherein R is an alicyclic group; an arylethyl group; or phenyl or benzyl substituted by halogen, lower alkyl, alkoxy, OH, $NH_2$, NHalkyl, $N(alkyl)_2$, CN or $NO_2$; in the manufacture of a medicament for the therapy of hyperalgesic pain conditions and their symptoms.

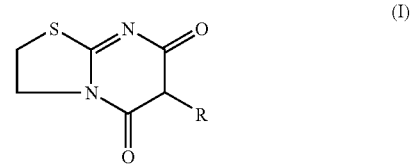

12 Claims, No Drawings

THIAZOLOPYRIMIDINES FOR USE IN THERAPY

This application is a National Stage Application of International Application Number PCT/GB2006/002248, filed Jun. 19, 2006; which claims priority to Great Britain Application No. 0512554.7, filed Jun. 20, 2005.

FIELD OF THE INVENTION

The present invention relates to the therapeutic use of thiazolopyrimidines, in the treatment of hyperalgesic pain conditions and their symptoms.

BACKGROUND TO THE INVENTION

Hyperalgesic pain conditions are conditions of heightened pain perception caused by tissue damage. These conditions are a natural response of the nervous system apparently designed to encourage protection of the damaged tissue by an injured individual, to give time for tissue repair to occur. The symptoms of hyperalgesic pain conditions include hyperalgesia, allodynia (tactile, thermal) and paresthesia. Hyperalgesia is an abnormal pain response to a pain stimulus. Allodynia is a condition where a normal stimulus causes pain. Paresthesia is an abnormal sensation of the skin such as numbness, tingling, pricking, burning, crawling with no objective cause. There are two known underlying causes of these conditions, an increase in sensory neuron activity, and a change in neuronal processing of nociceptive information which occurs in the spinal cord. These conditions can be debilitating in chronic inflammation and when sensory nerve damage has occurred (i.e. neuropathic pain). As mentioned above, hyperalgesic pain conditions are a consequence in most instances of tissue damage, either damage directly to a sensory nerve, or damage of the tissue innervated by a given sensory nerve.

Diseases involving damage to sensory nerves which contain a component of neuropathic pain include, but are not limited to, diabetic neuropathy, cancer pain, fibromyalgia, myofascial pain syndrome, osteoarthritis, pancreatic pain, pelvic/perineal pain, post-herpetic neuralgia, complex regional pain syndrome, sciatica/lumbar radiculopathy, spinal stenosis, temporo-mandibular joint disorder, HIV pain, trigeminal neuralgia, chronic neuropathic pain, lower back pain, failed back surgery pain, post-operative pain, post-physical trauma pain (including gunshot, RTA, burns), cardiac pain, chest pain, pelvic pain/pid, joint pain (tendonitis, bursitis, acute arthritis), neck pain, obstetric pain (labour/C-section), renal colic, acute herpes zoster pain, acute pancreatitis, breakthrough pain (cancer) and dysmenorhoea/endometriosis.

Two major classes of analgesics are known: (i) non-steroidal anti-inflammatory drugs (NSAIDs) and the related COX-2 inhibitors; and (ii) opiates based on morphine. Analgesics of both classes are reasonably effective in controlling normal, immediate or nociceptive pain. However, they are less effective against some types of hyperalgesic pain, such as neuropathic pain. Many medical practitioners are reluctant to prescribe opiates at the high doses required to affect neuropathic pain because of the side-effects caused by administration of these compounds, and the possibility that patients may become addicted to them. NSAIDs are much less potent than opiates, so even higher doses of these compounds are required. This is, however, undesirable because these compounds cause irritation of the gastro-intestinal tract.

There is, therefore, a need for anti-hyperalgesics and neuropathic pain treatments which are sufficiently potent to control pain perception in neuropathic and other hyperalgesic syndromes, and which do not have serious side-effects or cause patients to become addicted to them.

EP-A-0050671 describes thiazolo[3,2-a]pyrimidine derivatives of formula (I)

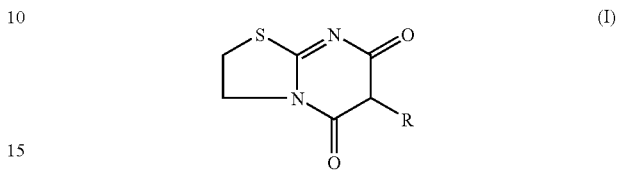

which exhibit immuno-regulating properties and are useful as agents for curing autoimmune diseases such as nephritis and rheumatoid arthritis. One particular compound of formula (I) is 6-(p-chlorobenzyl)-5H-2,3,6,7-tetrahydro-5,7-dioxothiazolo[3,2-a]pyrimidine, otherwise known as nuclomedone and hereinafter referred to as Compound 1, the chemical structure of which is:

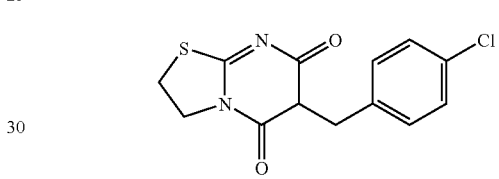

Compound 1 was originally developed as a potential treatment for rheumatoid arthritis or nephritis, but has now been discontinued in these indications. In preclinical studies, nuclomedone restored kidney function in mice with autoimmune neuropathy and inhibited lipopolysaccharide-induced polyclonal antibody responses.

SUMMARY OF THE INVENTION

A first aspect of the invention is the use of a compound of formula (I):

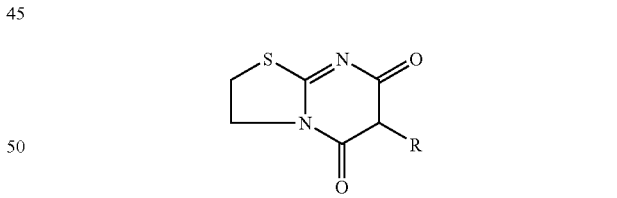

wherein R is an alicyclic group; an arylethyl group; or phenyl or benzyl substituted by halogen, lower alkyl, alkoxy, OH, $NH_2$, NHalkyl, $N(alkyl)_2$, CN or $NO_2$;

in the manufacture of a medicament for the therapy of hyperalgesic pain conditions and their symptoms.

An alternative expression of the invention is a method for the treatment of hyperalgesic pain in a patient in need thereof, which comprising administering to the patient an effective amount of a compound of formula (I).

It has been found that, after administration of a compound of formula (I), no effect on normal physiological nociception was observed and thus, when such compounds are used to treat hyperalgesia, there is no reduction in normal sensory perception.

DESCRIPTION OF THE INVENTION

The term "halogen" as used herein includes a fluorine atom, a chlorine atom, a bromine atom and an iodine atom.

The term "alkyl" as used herein refers to a straight or branched chain unsaturated aliphatic moiety, and includes, for example, methyl, ethyl, propyl, iso-propyl, butyl, tert-butyl, pentyl, hexyl and the like. "Lower alkyl" refers to an alkyl group containing 1 to 6 carbon atoms.

The term "alkoxy" as used herein refers to an alkyl group as defined above attached through an oxygen atom. It includes, but is not limited to, methoxy, ethoxy, propoxy, isopropoxy, butoxy, tert-butoxy, pentoxy, hexoxy and the like. "Lower alkoxy" refers to an alkoxy group containing 1 to 6 carbon atoms.

The term "aryl" as used herein refers to optionally substituted aromatic ring systems, and optionally substituted polycyclic ring systems having two or more cyclic rings, at least one of which is aromatic. This term covers, for example, phenyl.

The term "arylethyl" as used herein refers to an aryl-substituted ethyl group.

The term "alicyclic" as used herein refers to a non-aromatic saturated cyclic moiety which may contain one or more non-conjugated double bonds. The group may optionally be substituted. It includes, but is not limited to, cyclopropyl, cyclobutyl, cyclopentyl, cycloheptyl, cyclohexyl, 2-methylcyclopropyl and the like.

A preferred compound for use in the present invention is 6-(p-chlorobenzyl)-5H-2,3,6,7-tetrahydro-5,7-dioxothiazolo[3,2-a]pyrimidine, i.e. compound 1.

The compounds for use in the invention may be present in two tautomeric forms as shown:

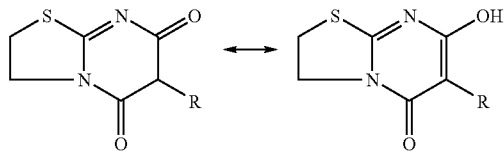

The compounds for use in the present invention may be chiral. They may be in the form of a single enantiomer, e.g. the (R) enantiomer substantially free of the opposite enantiomer, or vice versa, or a diastereomer (if the R group is chiral), or a racemate.

The compounds of the invention may be prepared in racemic form, or prepared in individual enantiomeric form by specific synthesis or resolution as will be appreciated in the art. The compounds may, for example, be resolved into their enantiomers by standard techniques, such as the formation of diastereomeric pairs by salt formation with an optically active acid followed by fractional crystallisation and regeneration of the free base. Alternatively, the enantiomers of the novel compounds may be separated by HPLC using a chiral column.

For use in the invention, a compound of formula may be given as a prodrug. As used herein, the term "prodrug" refers to compounds that are drug precursors which, following administration, release the drug in vivo via some chemical or physiological process. Further, compounds for use in the present invention may be in protected amino, protected hydroxy or protected carboxy form. The terms "protected amino", "protected hydroxyl" and "protected carboxy" as used herein refer to amino, hydroxy and carboxy groups which are protected in a manner familiar to those skilled in the art. For example, an amino group can be protected by a benzyloxycarbonyl, tert-butoxycarbonyl, acetyl or like group, or in the form of a phthalimido or like group. A carboxyl group can be protected in the form of a readily cleavable ester such as the methyl, ethyl, benzyl or tert-butyl ester. A hydroxy group can be protected by an alkyl or like group.

Some compounds of the formula may exist in the form of solvates, for example hydrates, which also fall within the scope of the present invention.

Compounds for use in the invention may be in the form of pharmaceutically acceptable salts, for example, addition salts of inorganic or organic acids. Such inorganic acid addition salts include, for example, salts of hydrobromic acid, hydrochloric acid, nitric acid, phosphoric acid and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl)benzoic acid, 1-hydroxy-2-naphthoic acid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulphuric acid, mucic acid, 2-naphthalenesulphonic acid, pamoic acid, pantothenic acid, phosphanilic acid ((4-aminophenyl)phosphonic acid), picric acid, salicylic acid, stearic acid, succinic acid, tannic acid, tartaric acid, terephthalic acid, p-toluenesulphonic acid, 10-undecenoic acid and the like.

Salts may also be formed with inorganic bases. Such inorganic base salts include, for example, salts of aluminium, bismuth, calcium, lithium, magnesium, potassium, sodium, zinc and the like. Organic base salts include, for example, salts of N,N-dibenzylethylenediamine, choline (as a counterion), diethanolamine, ethanolamine, ethylenediamine, N,N-bis(dehydroabietyl)ethylenediamine, N-methylglucamine, procaine, tris(hydroxymethyl)aminoethane ("TRIS") and the like.

It will be appreciated that such salts, provided that they are pharmaceutically acceptable, may be used in therapy. Such salts may be prepared by reacting the compound with a suitable acid or base in a conventional manner.

A compound for use in the invention may be prepared by any suitable method known in the art. Reference may be made to EP-A-0050671, the content of which is incorporated by reference.

Any mixtures of final products or intermediates obtained can be separated on the basis of the physico-chemical differences of the constituents, in a known manner, into the pure final products or intermediates, for example by chromatography, distillation, fractional crystallisation, or by the formation of a salt if appropriate or possible under the circumstances.

The activity and selectivity of the compounds may be determined by any suitable assay known in the art.

The present invention is directed to use of compounds of formula (I) in the manufacture of a medicament for the prevention, treatment or amelioration of hyperalgesic pain conditions and their symptoms.

The hyperalgesic pain conditions may be caused as a result of neuropathy, including, but not limited to, diabetic neuropathy, polyneuropathy, cancer pain, fibromyalgia, myofascial pain syndrome, osteoarthritis, pancreatic pain, pelvic/perineal pain, post herpetic neuralgia, complex regional pain syndrome, sciatica/lumbar radiculopathy, spinal stenosis, temporo-mandibular joint disorder, HIV pain, trigeminal neuralgia, chronic neuropathic pain, lower back pain, failed back surgery pain, post operative pain, post physical trauma pain (including gunshot, RTA, burns), cardiac pain, chest pain, pelvic pain/pid, joint pain (tendonitis, bursitis, acute arthritis), neck pain, bowel pain, phantom limb pain, obstetric pain (labour/C-section), renal colic, acute herpes zoster pain, acute pancreatitis, breakthrough pain (cancer), painful bladder syndrome/interstitial cystitis, prostatitis and dysmenorhoea/endometriosis.

A compound of formula (I) may be administered with or without other therapeutic agents, for example analgesics and anti-inflammatories (such as opiates, steroids, NSAIDs, cannabinoids, tachykinin modulators, or bradykinin modulators) or anti-hyperalgesics (such as gabapentin, pregabalin, cannabinoids, sodium or calcium channel modulators, anti-epileptics or anti-depressants).

In general, a compound of formula (I) may be administered by known means, in any suitable formulation, by any suitable route. A compound of the invention is preferably administered orally, parenterally, sublingually, transdermally, intrathecally, or transmucosally. Other suitable routes include intravenous, intramuscular, subcutaneous, inhaled, nasal, rectal, topical and intravesically. The amount of drug administered will typically be higher when administered orally than when administered, for example, intravenously.

The compositions may be formulated in a manner known to those skilled in the art so as to give a controlled release, for example rapid release or sustained release, of the compounds of the present invention. Pharmaceutically acceptable carriers suitable for use in such compositions are well known in the art. The compositions of the invention may contain 0.1-99% by weight of active compound. The compositions of the invention are generally prepared in unit dosage form. Preferably, a unit dose comprises the active ingredient in an amount of 0.1 to 1000 mg. The excipients used in the preparation of these compositions are the excipients known in the art.

Appropriate dosage levels may be determined by any suitable method known to one skilled in the art. It will be understood, however, that the specific dose level for any particular patient will depend upon a variety of factors including the activity of the specific compound employed, the age, body weight, general health, sex, diet, time of administration, route of administration, rate of excretion, drug combination and the severity of the hyperalgesia. Preferably, a compound of structure (I) is administered at a frequency of 1 to 4 times per day.

Compositions for oral administration include known pharmaceutical forms for such administration, for example tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example corn starch or alginic acid; binding agents, for example starch gelatin, acacia, microcrystalline cellulose or polyvinyl pyrrolidone; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long-chain aliphatic alcohols, for example heptadecaethyleneoxycetanol, or condensation products of ethylene oxide with partial esters derived from fatty acids, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, polyoxyethylene hydrogenated castor oil, fatty acids such as oleic acid, or in a mineral oil such as liquid paraffin or in other surfactants or detergents. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in a mixture with a dispersing or wetting agent, suspending agent and one or more preservatives. Suitable sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin, or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid, find use in the preparation of injectables.

The compounds for use in the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for topical administration are also suitable for use in the invention. The pharmaceutically active compound may be dispersed in a pharmaceutically acceptable cream, ointment or gel. A suitable cream may be prepared by incorporating the active compound in a topical vehicle such as light liquid paraffin, dispersed in a aqueous medium using surfactants. An ointment may be prepared by mixing the active compound with a topical vehicle such as a mineral oil or wax. A gel may be prepared by mixing the active compound with a topical vehicle comprising a gelling agent. Topically administrable compositions may also comprise a matrix in which the pharmaceutically active compounds of the present invention are dispersed so that the compounds are held in contact with the skin in order to administer the compounds transdermally.

Compounds of formula (I) can be used for the treatment of pain caused as a result of neuropathy or inflammatory disease (or a combination of both) including, but not limited to diabetic neuropathy, polyneuropathy, cancer pain, fibromyalgia, myofascial pain syndrome, osteoarthritis, pancreatic pain, pelvic/perineal pain, post herpetic neuralgia, complex regional pain syndrome, sciatica/lumbar radiculopathy, spinal stenosis, temporo-mandibular joint disorder, HIV pain, trigeminal neuralgia, chronic neuropathic pain, lower back/pain, failed back surgery pain, post-operative pain, post-physical trauma pain (including gunshot, RTA, burns), cardiac pain, chest pain, pelvic pain/pid, joint pain (tendonitis, bursitis, acute arthritis), neck pain, bowel pain, phantom limb pain, obstetric pain (labour/C-section), renal colic, acute herpes zoster pain, acute pancreatitis breakthrough pain, cancer pain, dysmenorrhoea/endometriosis, painful bladder syndrome/interstitial cystitis, prostatitis, osteoarthritis, rheumatoid spondylitis, gouty arthritis, and other arthritic conditions, cancer, HIV, chronic pulmonary inflammatory disease, silicosis, pulmonary sarcosis, bone resorption diseases, reperfusion injury (including damage caused to organs as a consequence of reperfusion following ischaemic episodes, e.g. myocardial infarcts, strokes), autoimmune damage (including multiple sclerosis, Guillam-Barre syndrome, myasthenia gravis), graft v. host rejection, allograft rejections, fever and myalgia due to infection, AIDS-related complex (arc), keloid formation, scar tissue formation, Crohn's disease, ulcerative colitis and pyresis, irritable bowel syndrome, osteoporosis, cerebral malaria and bacterial meningitis.

The following Examples provide evidence on which the present invention is based. They utilise models reported in the following references:

Bennett, G J and Xie, Y K (1988), "A peripheral mononeuropathy in rat that produces disorders of pain sensation like those seen in man", Pain 33:87-107.

Brennan T J, Vandermeulen E P and Gebhart G F (1996), "Characterization of rat model of incisional pain", Pain 64:493-501.

Example 1

Single Oral Dose Study in the Rat Chronic Constriction Injury (CCI) Model

Surgery

The rat chronic constriction injury (CCI) model was prepared following the standard protocols (Bennett and Xie, 1988). Briefly, male Sprague-Dawley rats, weighing 150-175 gram at arrival, were anaesthetized with a 5% isofluorane/95% oxygen gas mixture followed by an i.p. injection of sodium pentobarbitone (50 mg/kg). The lateral side of the left hind limb was shaved and sterilized with 75% ethanol. An incision of about 1 cm was made to expose the sciatic nerve. Four loose ligations with 4-0 suture silk were made on the sciatic nerve. The wound was closed in layers with silk suture and the animals were placed in a recovering chamber with the temperature controlled at 30° C. The animals were then returned to their home cage after complete return of consciousness and the return of free movement. A dose of amoxicillin (0.1 ml, 15 mg) was routinely injected intraperitoneally after surgery to prevent infection.

Behavioural Test (Mechanical Allodynia)

In CCI rats, the assessment of paw withdrawal threshold (PWT) in response to the mechanical stimulation started 14 days after surgery. The baseline thresholds were measured for 3 consecutive days before and 0.5, 1, 2, 3 and 4 hours after drug application. The PWT was measured using a series of graduated von Frey hairs. The animals were placed in individual perspex boxes on a raised metal mesh for at least 30 min before the test. Starting from a filament of lower force (1 g), each filament was applied perpendicularly to the centre of the paw pad until it slightly bends for 6 seconds. If the animal withdrew or lifted the paw upon stimulation, then a hair with force immediately lower than that tested would be used. If no response was observed, then a hair with force immediately higher would be used. The lowest amount of force required to induce reliable responses (positive in 3 out of 5 trials) was recorded as the value of PWT.

Drug Preparation

A suspension of Compound 1 was made with 5% DMSO in saline (10 mg/ml). The suspension was sonicated for at least 20 min before application.

Results

All data in this study are presented as mean±S.E.M. and are analysed with the student-t-test or one way ANOVA as appropriate. The significance level was set at $P<0.05$.

Vehicle controls: paw withdrawal thresholds (PWT) were tested before and at 0.5, 1, 2, 3 and 4 hours after vehicle oral (p.o.) dosing. Over the time points observed, there were no significant changes observed in different vehicle control groups. No vehicle control PWT measurement was made at the 6 hour time point.

Oral application of Compound 1, at a dose of 20 mg/kg, significantly increased the PWT in the CCI rats at multiple time points, 2, 3 and 4 hours after dosing. At 2, 3 and 4 hours, the PWT were 2.6±0.7 g, 3.0±0.7 g and 6.3±0.8 g, $P<0.05$, 0.01 and 0.001, compared to the PWT at the same time points of the vehicle treated group. The effect of the compound lasted longer than 6 hours (4.0±0.5 g, $P<0.001$ compared to the pre-dosing control).

The above results suggest that Compound 1 is orally bioavailable and has a significant effect in relieving neuropathic pain state at a dose of 20 mg/kg p.o. in the CCI model.

Example 2

Dose-Response Study in CCI Model

The methods for preparing CCI animals and assessing mechanical allodynia using von Frey hairs were as described in Example 1. Four doses of Compound 1 (1, 3, 10, 30 mg/kg) were given orally and the PWT was reassessed at 30, 60, 120, 180, 240 and 360 min after dosing.

It was found that Compound 1 dose-dependently increased the PWT in CCI rats. One-way ANOVA analysis revealed that there are significant difference between different dose groups at 120 ($P<0.05$), 180, 240 and 360 min ($P<0.001$). Post-hoc analysis shows that there are significant differences between different dose groups at 180, 240 and 360 min after oral administration of Compound 1.

The results indicate Compound 1 reverses the allodynia generated in CCI rats in a dose-dependent manner. The results suggest that this compound may be useful in treating nerve injury-induced neuropathic pain states.

Example 3A

Effects of Acute Administration on Ectopic Discharge in CCI Rats

Spontaneous ectopic discharge in peripheral nerve is a characteristic phenomenon in neuropathic pain animal models. It is considered to be responsible for generation and maintenance of spinal sensitization and neuropathic states. Therefore, if a compound has effect in inhibiting ectopic discharge, it may be useful in treating neuropathic pain states.

The preparation of CCI model rats and the assessment of neuropathic pain state were as described for Example 1. The electrophysiological experiments were performed on CCI rats with neuropathic pain states confirmed by von Frey hair testing as previously described. Compound 1 suspension was made in a vehicle containing 1% DMSO, 66% PEG200 and 33% saline to 5 mg/ml.

Rats with neuropathic pain were anaesthetized with thiobutabarbital sodium (inactin, 120 mg/kg, i.p. for induction and thereafter 60 mg/kg, i.p. for maintenance, if necessary). The arterial blood pressure and heart rate were routinely monitored and rectal temperature was continuously monitored and maintained at a physiological range using a thermo-blanket system.

The skin of the left hind limb was incised and stitched onto a stainless steel "O" ring to form an oil pool. The sural nerve was carefully exposed and repeatedly teased into small bundles containing only one or a few fibres and examined for spontaneous activity. In acute experiments, when an active fibre was found, a period of at least 20 min control recording was obtained. Subsequently, the effects of the vehicle and Compound 1 (5 mg/kg, i.v.) were examined. Activity was monitored for at least 40 minutes following administration of the drug. The frequency of the spontaneous activity was monitored online and analysed offline after experiment.

For i.v. injection, Compound 1 suspension (5 mg/ml) was prepared using a vehicle made of 1% DMSO, 66% polyethelene glycol (PEG 200) and 33% normal saline. The suspension was then sonicated for 30 min before administration.

The effect of vehicle and Compound 1 (5 mg/kg i.v.) was tested in two separate CCI preparations. In the first preparation, the vehicle reduced the ectopic discharge from 682 imps/min to 591, whilst Compound 1 (5 mg/kg i.v.) reduced the ectopic discharge from 682 imps/min to 426. In the second preparation, the ectopic discharge was reduced from 298 imps/min to 215 and 104 after iv injection of vehicle and Compound 15 mg/kg, respectively.

In four fibres, the average firing rate of ectopic discharge before drug application was 489.7±125.8 imps/min (ranged from 248 to 730 imps/min). After injection of vehicle, it was slightly but not statistically reduced to 440±129.0 imps/min (87.6.8% of control, $P>0.05$); after administration, the firing rate of ectopic discharge was significantly reduced to 307.6±113.4 imps/min (57.1±9.0% of control, $P<0.01$).

From these two experiments, it appears that Compound 1 (5 mg/kg i.v.) is effective in reducing the spontaneous ectopic discharge measured in the rat peripheral nerve following establishment of CCI induced neuropathy.

Example 3B

Effect of Chronic Dosing on Generation of Ectopic Discharge in CCI Rats

After confirmation of neuropathic pain state on day 16 post-surgery, the animals (4 for vehicle group and 4 for drug treatment group) were given either vehicle (5% DMSO in saline) or Compound 130 mg/kg p.o., twice a day for 8 days. At the end of the dosing protocol, the PWT was reassessed before the electrophysiological experiment.

The sural nerve was repeatedly teased into fine bundles for examination. For a fibre with spontaneous activity, the recording lasted for at least 1 min; for a fiber without obvious spontaneous activity, the recording lasted for at least 30 sec. In each sural nerve, as many fibres as possible were teased and recorded (more than 150 bundles on average in one animal).

In 4 CCI rats, after 8 days of treatment with Compound 1, the PWT was significantly higher than that in vehicle-treated.

In the vehicle-treated group, 602 fibres from 4 rats were examined. Among those fibres, 197 fibres had spontaneous activity. In contrast, among 633 fibres recorded from 4 rats treated with Compound 1, there were only 48 fibres with spontaneous activity. The proportion of 'active fibres' was significantly lower in DRP-treated group than that in vehicle group ($P<0.001$, $\chi^2$ test).

In vehicle-treated rats, the spontaneous activity ranged from 15 to 3905/min with averaged frequency 1123.5±69.4. In the Compound 1-treated group, the frequency of spontaneous activity ranged from 13 to 3532/min (averaged frequency was 888.9±148.5/min). However, a comparison of averaged frequency of spontaneous activity failed to reveal significant difference between vehicle and Compound 1 groups.

Chronic treatment of CCI rats with Compound 1 significantly reduced the proportions of fibres with spontaneous activity. The results suggest that Compound 1 may prevent the generation and maintenance of ectopic discharge in CCI rats, therefore leading to the relief of neuropathic pain conditions.

Example 4

Tolerance Liability in CCI Model

The preparation of CCI model rats and the assessment of neuropathic pain state using von Frey hairs were as the same as described for Example 1. The PWT was assessed in the morning for 3 consecutive days prior to the surgery and on days 6, 14, 15 and 16 after surgery. Starting from day 16, the animals were either dosed with vehicle (5% DMSO in saline, 1 ml/kg) or Compound 1 30 mg/kg p.o., twice a day for 7 days. From day 16 onward, PWT was assessed thereafter every morning and 4 hours after dosing, up to day 23 post surgery.

On day 16 after surgery, the baseline PWT was significantly lowered to the level measured prior to surgery (11.86±0.43 g in vehicle group pre-surgery, n=7, and 10.75±0.35 in Compound 1 group pre-surgery, n=8) to 1.23±0.03 g (vehicle group) and 1.15±0.07 g on day 16 post surgery. The baseline PWT after the first day's treatment was higher than that observed in the vehicle group, and remained at a higher level throughout the 7 day experiment dosing period. Interestingly, the baseline in the Compound 1 group was raised over the 7 day treatment period. Therefore, the magnitude of PWT increase, in comparison to baseline, in the Compound 1 group was reduced in comparison to that seen in the first day of treatment.

There was no significant loss of efficacy of Compound 1 in reversing lowered PWT over 7 days of treatment. In addition, the baseline measurement, taken each morning prior to giving the first daily dose, was raised over the course of the experiment. This suggests that, far from losing efficacy over the course of this chronic dosing study, on repeat dosing Compound 1 is able to alleviate CCI-induced mechanical allodynia for as long as 12 hours post-dose.

Example 5

Effect on PWT in Rats with Diabetic Neuropathy

Under isofluorane anaesthesia, adult male Sprague-Dawley rats (150-200 g) were given an intraperitoneal injection of streptozotocin (75 mg/kg, Calbiochem). After injection, particular care was taken to ensure that water and food were available at all time and the beddings were changed frequently. A week after streptozocin injection, the blood glucose content was examined using Advantage II with Accutech strips (Roche). Only rats with blood glucose higher than 12 mM/L (216 mg/DL) were chosen for behavioural study.

The assessment of neuropathic pain state using von Frey hairs was the same as described for Example 1. Rats with lowered PWT (<4 g) were used for either vehicle (1 ml/kg, p.o. or Compound 1 (1, 3, 10, and 30 mg/kg p.o.) dosing. The PWT was reassessed at 1, 2, 3, 4 and 6 hours after oral dosing.

Neither vehicle or Compound 1 at 1 mg/kg produced significant changes in PWT. However, at doses higher than 3 mg/kg p.o., Compound 1 significantly increased the PWT in rats with diabetic neuropathy. This effect is dose-dependent. The results suggest that Compound 1 may have potential therapeutic effect in treating diabetic neuropathy.

Example 6

Effect on PWT in the Rat Brennan Model of Surgical Pain

The surgical pain model was prepared as described by Brennan et al (1996). Briefly, the rat was anaesthetised with 5% isofluorane in oxygen (2 L/min) for induction followed by an intravenous injection of sodium pentobarbitone (50 mg/kg) prior to surgery. The surgery was carried out under aseptic routines. The left hind paw was sterilized with 75% ethanol solution. A 1.5 cm longitudinal incision was made with a scalpel from about 0.5 cm of the heel edge towards the toes. The plantaris muscle and fascia were elevated and incised longitudinally but the structure of these tissues kept intact. After complete hemostasis with pressure, the skin was closed with stitches of 5-0 suture silk. The animal was routinely given an intraperitoneal injection of Amoxipen 15 mg/kg for prevention of infection after surgery. After surgery, the animals were placed in a temperature-controlled recovering chamber until full return of conscience and voluntary movement, before being returned to their home cages.

Neither vehicle (n=8) or Compound 1 at 3 mg/kg (n=7) produced significant changes in PWT (P>0.05). However, at doses higher than 3 mg/kg p.o., Compound 1 significantly increased the PWT in rats that had undergone the induction of surgical pain. This effect was dose-dependent. At 4 hours post-surgery, Compound 1 at 10 mg/kg and 30 mg/kg significantly raised the PWT from control level (1.50±0.36 g and 1.82±3.8 g respectively) to 2.60±0.48 g and 3.80±0.44 g, respectively (P<0.05 and 0.001, respectively). The analgesic effect of the 10 mg/kg dose had gone after 6 hours. However, the effects of the 30 mg/kg dose were still evident at 8 hours after post-dose (6 hours, 5.28±0.66 g and 8 hours, 4.16±0.79 g, P<0.001, compared to the vehicle group at the same time points).

A characteristic phenomenon observed in this surgical pain model study was that the effect of Compound 1 in enhancing PWT appeared later than that in either the CCI model or in the diabetic model. The effect was not observed until 4 hours after dosing and lasted up to 8 hours after dosing.

Thus, Compound 1 dose-dependently increases the PWT in the Brennan model of surgical pain. The results suggest that Compound 1 may have potential therapeutic effects in treating clinical surgical pain. The reason for delayed analgesic effect observed in this model is unknown.

The invention claimed is:

1. A method for treating neuropathic pain conditions and their symptoms, wherein said method comprises administering, to a patient in need of such treatment, a compound of formula (1)

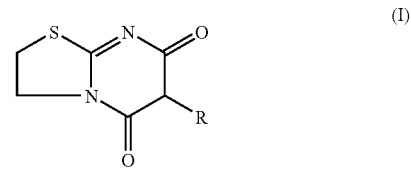

wherein R is an alicyclic group; an arylethyl group; or phenyl or benzyl substituted by halogen, lower alkyl, alkoxy, OH, $NH_2$, NHalkyl, $N(alkyl)_2$, CN or $NO_2$.

2. The method according to claim 1, wherein the neuropathic pain is caused by diabetic neuropathy.

3. The method according to claim 1, wherein the neuropathic pain is back pain.

4. The method according to claim 1, wherein the pain is fibromyalgia pain.

5. The method according to claim 1, wherein the pain is HIV pain.

6. The method according to claim 1, wherein the pain is complex regional pain syndrome.

7. The method according to claim 1, wherein the pain is trigeminal neuralgia or temporo-mandibular joint disorder.

8. The method according to claim 1, wherein the pain is post-herpetic neuralgia.

9. The method according to claim 1, wherein the pain is painful bladder syndrome/interstitial cystitis, prostatitis or dysmenorhoea/endometriosis.

10. The method according to claim 1, wherein the pain is selected from bowel pain, cancer pain, phantom limb pain, post-operative pain, polyneuropathy, myofascial pain syndrome, osteoarthritis, pancreatic pain, pelvic/perineal pain, sciatica/lumbar radiculopathy, spinal stenosis, chronic neuropathic pain, failed back surgery pain, post-physical trauma pain (including gunshot, rta, burns), post-operative pain, cardiac pain, chest pain, pelvic pain/pid, joint pain (tendonitis, bursitis, acute arthritis), neck pain, obstetric pain (labour/c-section), renal colic, acute herpes zoster pain, acute pancreatitis and breakthrough pain.

11. The method according to claim 1, wherein R is alicyclic, arylethyl, or phenyl or benzyl substituted by halogen, alkyl or alkoxy.

12. The method according to claim 11, wherein the compound is 6-(p-chlorobenzyl)-5H-2,3,6,7-tetrahydro-5,7-dioxothiazolo[3,2-a]pyrimidine.

* * * * *